US00PP14304P39

(12) United States Plant Patent
Manichote

(10) Patent No.: US PP14,304 P3
(45) Date of Patent: Nov. 18, 2003

(54) CURCUMA PLANT NAMED 'LADDAWAN'

(50) Latin Name: *Curcuma hybrid*
Varietal Denomination: Laddawan

(75) Inventor: Pichai Manichote, Bangkok (TH)

(73) Assignee: Ladda Co., Ltd. (TH)

( * ) Notice: Subject to any disclaimer, the term of this patent is extended or adjusted under 35 U.S.C. 154(b) by 0 days.

(21) Appl. No.: 10/037,764

(22) Filed: Jan. 2, 2002

(65) Prior Publication Data

US 2003/0126659 P1 Jul. 3, 2003

(51) Int. Cl.[7] ..... A01H 5/00
(52) U.S. Cl. ..... Plt./263

(58) Field of Search ..... Plt./263

(56) References Cited

U.S. PATENT DOCUMENTS

PP12,866 P2 * 8/2002 Ben Zur et al. ..... Plt./226
PP12,881 P2 * 8/2002 Zur et al. ..... Plt./263

* cited by examiner

*Primary Examiner*—Bruce R. Campell
*Assistant Examiner*—W C Haas
(74) *Attorney, Agent, or Firm*—Christie, Parker & Hale, LLP

(57) ABSTRACT

A new and distinct cultivar of Curcuma named 'Laddawan' characterized by green bracts, purplish pink coma bracts on a cylindical inflorescence and florets with yellow labellum.

4 Drawing Sheets

Botanical classification: *Curcuma hybrid.*

BACKGROUND OF THE INVENTION

The present invention is directed to a new and distinct cultivar of Curcuma, botanically know as *Curcuma hybrid,* and having the cultivar name 'Laddawan'.

The new cultivar was a seedling among a progeny of *Curcuma alismatifolia*×*Curcuma* cf. *cordata,* selected by the inventor.

Asexual propagation of the new cultivar in Nakhon Pathom, Thailand by division and micro-propagation has demonstrated the uniformity and the stability throughout successive generations of this new Curcuma.

SUMMARY OF THE INVENTION

The following traits have been repeatedly observed in the new cultivar grown under 50% shade condition in Nakhon Pathom, Thailand which closely approximate those commonly used in commercial horticulral practice.

The features that in combination are believed to distinguish 'Laddawan' from other known cultivars of Curcuma include: long peduncle; purplish pink coma bracts, obovate bracts; oblong ovate leaves.

Plants of the new Curcuma can be compared to plants of the *Curcuma alismatifolia* 'Chiang Mai' (Unpatented) which are popular in the world market. Plants of the new Curcuma differ from plants of the cultivar 'Chiang Mai' in the following characteristics:

1. The labellum of the new Curcuma floret is yellow, instead of blue as found in 'Chiang Mai'.
2. The coma bract of the new Curcuma is elliptic and spacing apart from each other, instead of obovate and closing together as found in 'Chiang Mai'.
3. The leaf of the new Curcuma is oblong ovate, instead of elliptic as found in 'Chiang Mai'.

4. The lateral vein of the new Curcuma is pronounced, instead of diffused as found in 'Chiang Mai'.

BRIEF DESCRIPTION OF ILLUSTRATIONS

The accompanying color photographs illustrate the overall appearance of the new cultivar as true in color as possible in color illustration of this type.

DESCRIPTION OF THE NEW VARIETY

Figure 1:
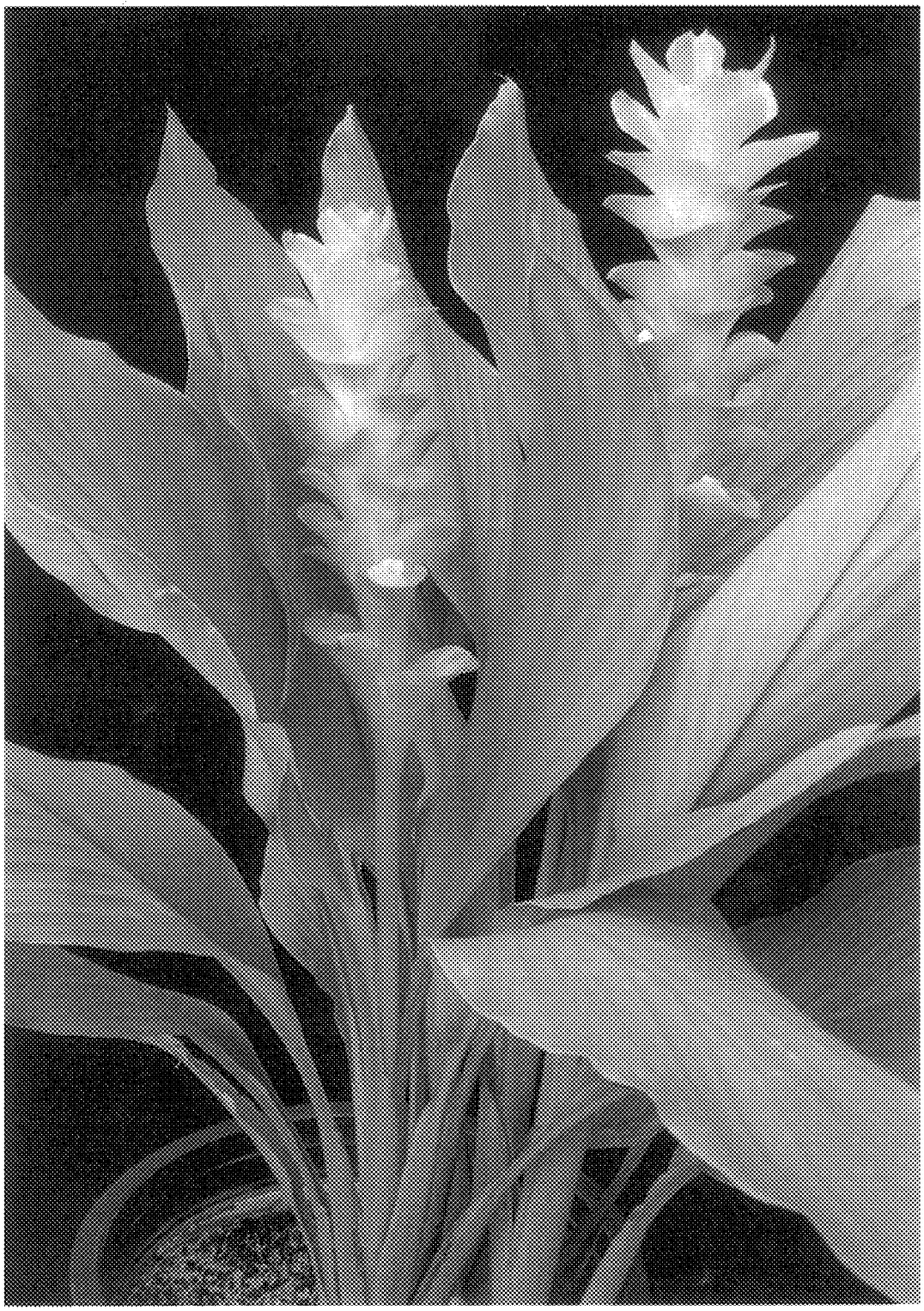
FIG. 1 is a side view of a full-grown plant of 'Laddawan,' illustrating both leaves, inflorescence and florets.
Figure 2:
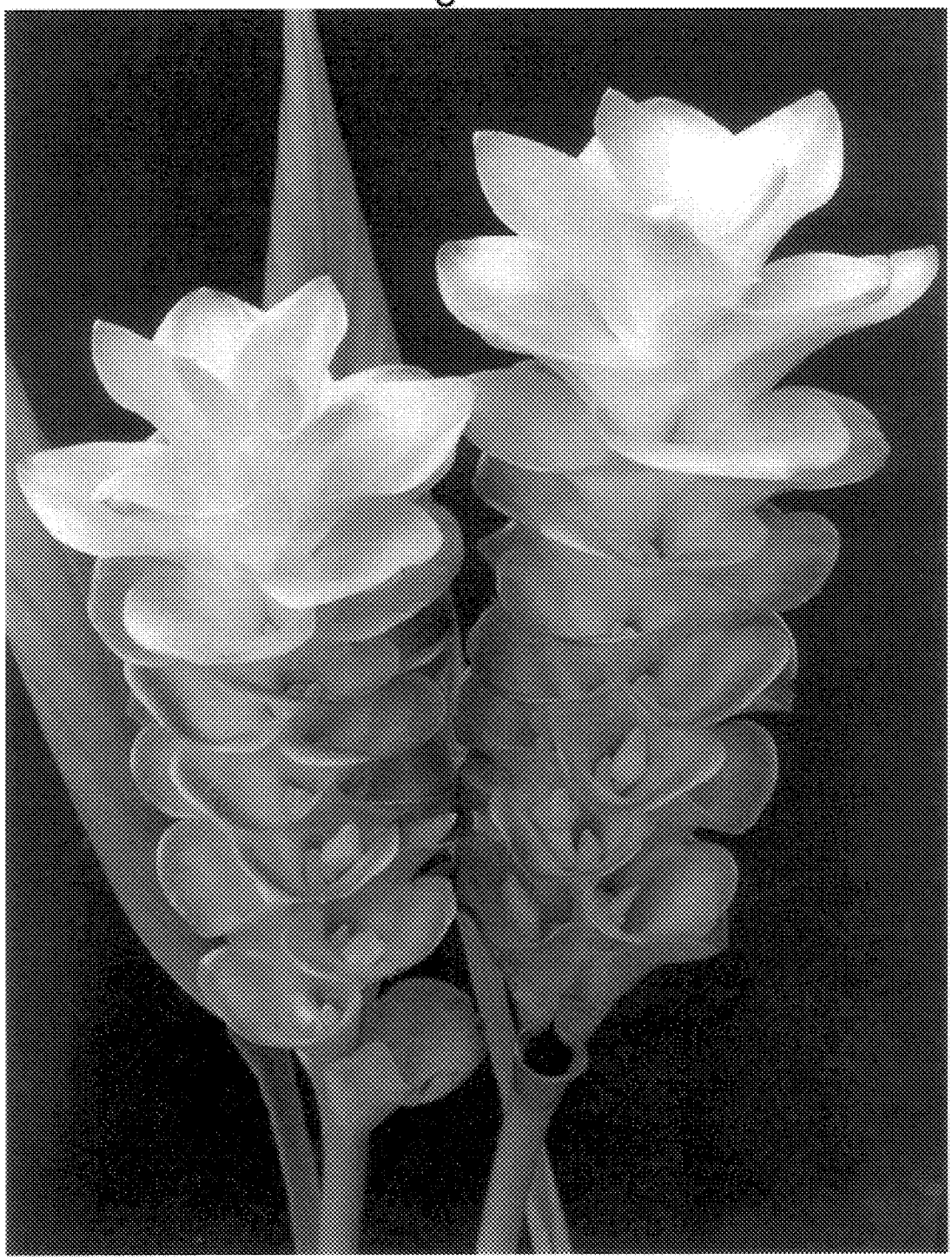
FIG. 2 is an inflorescence and florets of *Curcuma hybrids* 'Laddawan'.
Figure 3:
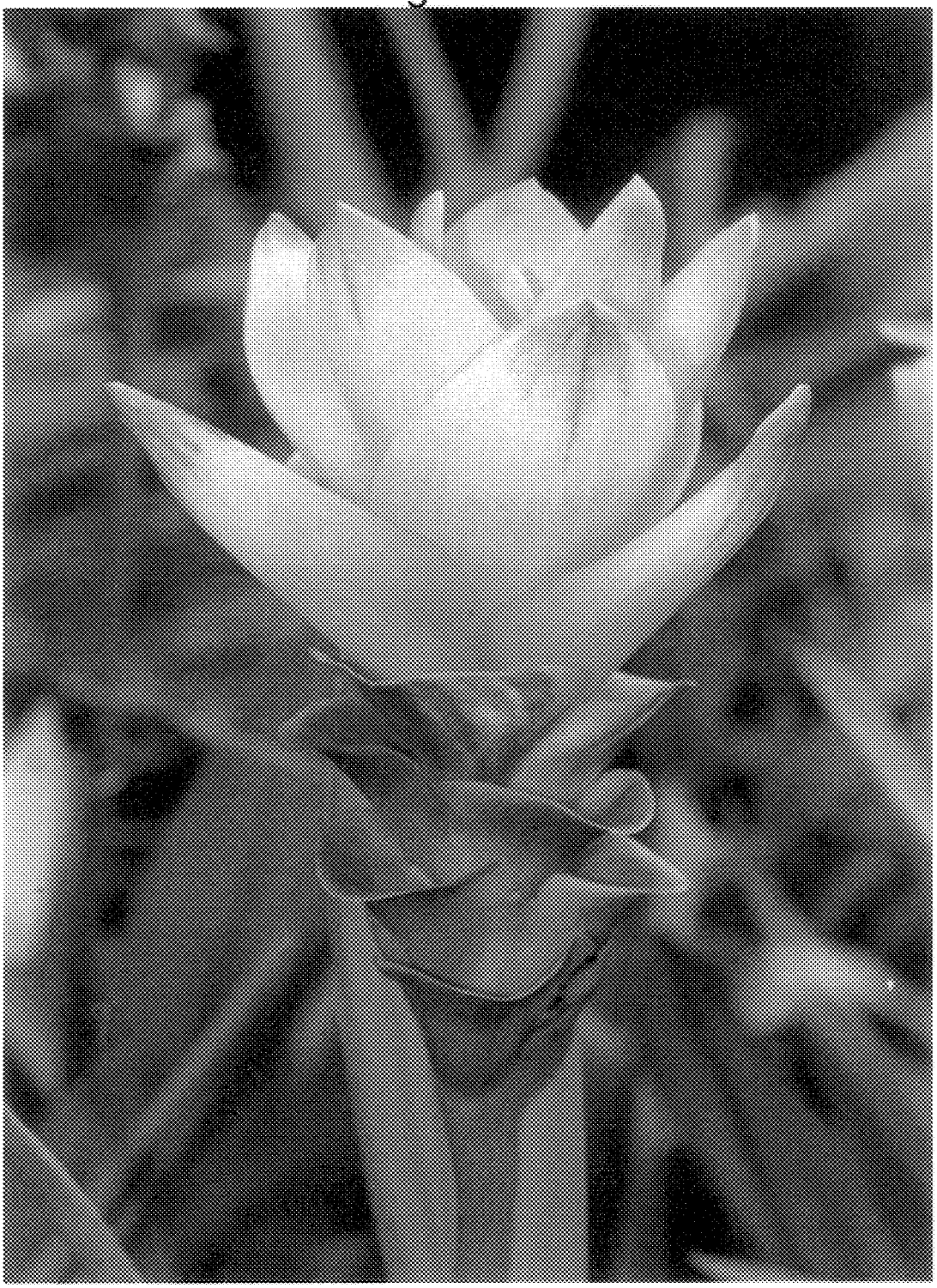
FIG. 3 is an inflorescence of *Curcuma alismatifolia* 'Chiang Mai.'
Figure 4:
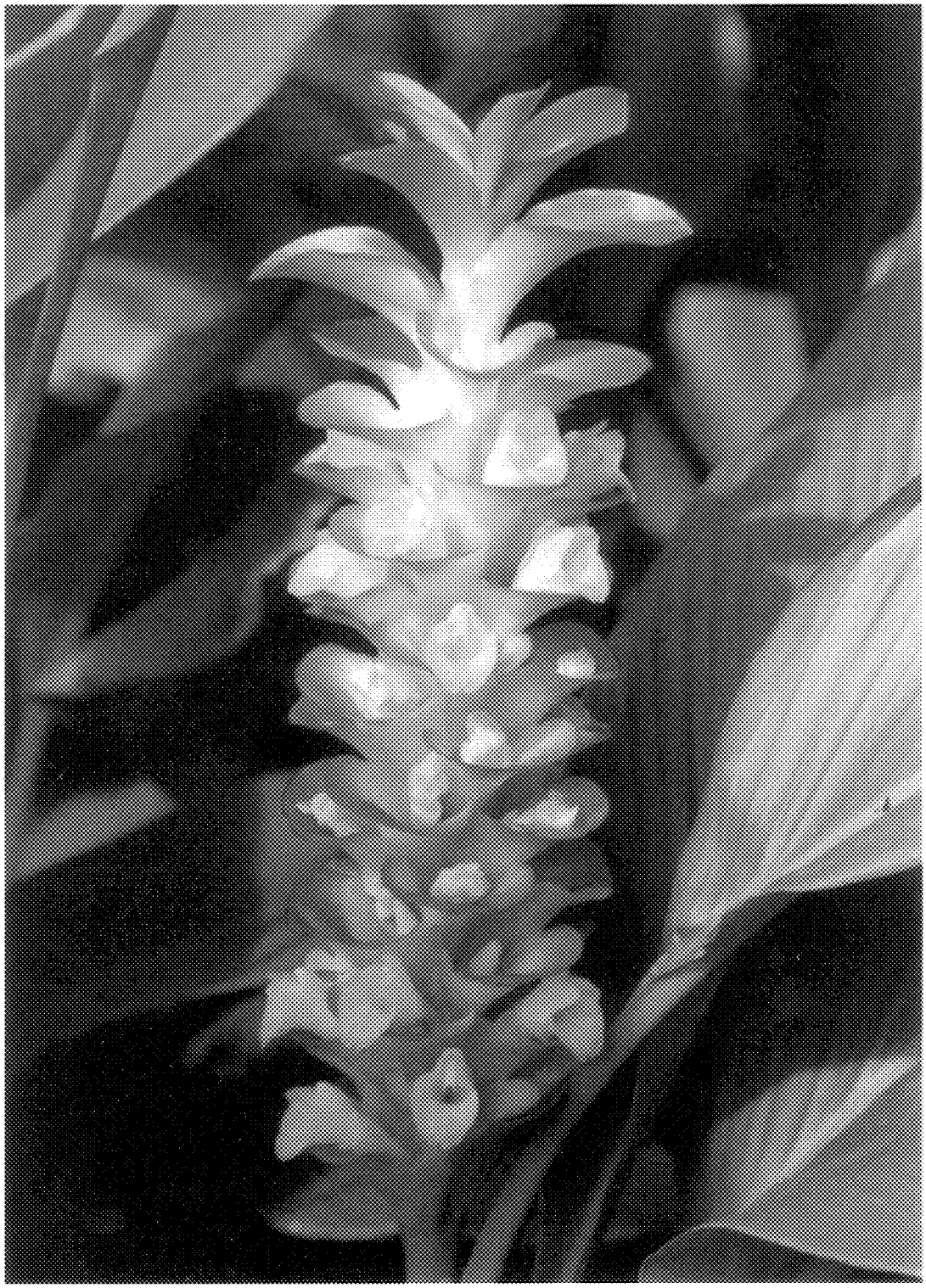
FIG. 4 is an inflorescence of *Curcuma* cf. *cordata.*

The following observations were made of 5-month old plants of the new variety grown under 50% shade conditions, in Nakhon Pathom, Thailand during the months of April through September. Phenotypic expression may vary with environmental, cultural and climatic conditions, as well as differences in conditions of light and soil.

Throughout this specification, color references and/or values are based upon The Royal Horticultural Society Colour Chart (1995 ed.) and terminology used in the color descriptions herein refers to plate numbers in this color chart except where common terms of color definition are employed.

Botanical classification: Curcuma hybrid 'Laddawan'.
Parentage:
*Female parent.—Curcuma alismatifolia.*
*Male parent.—Curcuma* cf. *cordata.*
Propagation: By division and micro-propagation. No fruit setting (sexually sterile).

Plant:

*Shape.*—Upright and clumping; Pseudostem upright and spreading.

*Growth habit.*—Resulting from branching of rhizome, the new pseudostem emerges close to the old pseudostem.

*Size.*—Height from soil surface to top of leaf canopy about 40 to 50 cm; height from soil surface to the highest leaf axil about 13 to 23 cm.

*Rhizome description.*—Corm-like; flesh near 4C.

*Diameter.*—About 2 to 3 cm.

*Height.*—About 2.2 to 4.5 cm.

*Vigor.*—Vigorous, rapid growth rate (multiplication rate of 7 to 16 folds per season).

*Root.*—Fibrous system with a number of storage roots.

*Disease resistance.*—Appears to be tolerant to Ralstonia wilt disease.

Foliage:

*Leaf shape.*—Oblong ovate with an attenuate apex; an obtuse base and an entire margin. Size: Length about 32 to 38 cm; width about 11.8 to 15.6 cm. Surface: Smooth with prounounced veins. Color: Upper Surface: Near 144A. Undersurface: Near 138B. Veins: Near 136B. Aspect: Distichous alternate array of leaf petiole on pseudostem. Erect initially, eventually arch outward.

*Petiole.*—Length about 2.4 to 4 cm; color near 143A.

Inflorescence: From Apical Bud of Pseudostem; cylindrical with open top; green bracts and purplish pink coma bracts.

*Peduncle.*—About 13.5 to 22 cm long, color green near 143C.

*Rachis.*—About 17.5 to 22.7 cm long and about 5 to 7.7 cm diameter.

*Bracts.*—Waxy coma bracts and bracts; obovate; between 12 to 17 coma bracts, coma bract color near 75A; 18 to 27 bracts, bract color near 144C; adaxial edge near 182C.

*Floret.*—About 3.7 to 4 cm long; crest tip; yellow labellum near 4D with dark yellow gills near 3A; bud color near 14D.

*Calyx tube.*—About 1 to 1.2 cm long with 3 lobes, color near 158D.

*Corolla tube.*—About 1.9 to 2.2 cm long with 3 unequal lobes, color near 158D, smaller side lobe; side staminode near 4D, about 1.4 to 1.7 cm long, 0.9 to 1 cm wide.

*Labellum.*—About 1.7 to 1.9 cm wide, color near 4D, gills near 3A, crest tip; anther with distal anther crest.

Plant of the Curcuma cultivar 'Laddawan' is upright and clumping. The inflorescence, from pseudostem apex, is cylindical with open top and has green bracts and purplish pink coma bracts. Floret has a yellow labellum with dark yellow gills.

I claim:

1. A new and distinct plant of *Curcuma hybrid* named 'Laddawan' substantially as illustrated and described.

* * * * *